US006937892B2

(12) United States Patent  
Leyde et al.

(10) Patent No.: US 6,937,892 B2
(45) Date of Patent: *Aug. 30, 2005

(54) METHOD AND APPARATUS FOR SECURING AND/OR IDENTIFYING A LINK TO A PERCUTANEOUS PROBE

(75) Inventors: Kent Leyde, Sammamish, WA (US); John F. Harris, Bellevue, WA (US); Paul C. Leonard, Woodinville, WA (US); Bradford Evan Gliner, Sammamish, WA (US)

(73) Assignee: Meagan Medical, Inc., Reno, NV (US)

( * ) Notice: Subject to any disclaimer, the term of this patent is extended or adjusted under 35 U.S.C. 154(b) by 392 days.

This patent is subject to a terminal disclaimer.

(21) Appl. No.: 10/260,202

(22) Filed: Sep. 27, 2002

(65) Prior Publication Data

US 2003/0065369 A1 Apr. 3, 2003

Related U.S. Application Data

(60) Provisional application No. 60/325,975, filed on Sep. 28, 2001.

(51) Int. Cl.[7] .............................................. A61N 1/00
(52) U.S. Cl. ............................................................ 607/2
(58) Field of Search ................................ 607/2, 58–63, 607/99, 116, 149

(56) References Cited

U.S. PATENT DOCUMENTS

| 5,224,475 A | 7/1993 | Berg et al. ................... 128/419 |
| 5,697,955 A | 12/1997 | Stolte ............................. 607/5 |
| 2001/0021869 A1 | 9/2001 | Bishay et al. ............... 607/116 |

FOREIGN PATENT DOCUMENTS

| FR | 2 653 023 | 10/1989 |
| WO | WO 01/39829 | 6/2001 |

*Primary Examiner*—George Manuel
(74) *Attorney, Agent, or Firm*—Blank Rome LLP (57) ABSTRACT

A method and apparatus for administering percutaneous electrical therapy to a recipient. The apparatus can include an electrical coupler having a coupling member configured to be removably positioned at least proximate to a percutaneous probe. The coupling member can be coupleable to a source of therapeutic electrical signals via a therapeutic signal transmission link to transmit the therapeutic electrical signals to the recipient. The apparatus can further include a status signal transmission link at least proximate to the therapeutic signal transmission link and coupleable to a status signal emitter. The status signal transmission link can be at least tamper-resistant and/or tamper-evident, and can be configured to transmit a status signal having a first characteristic value when the status signal transmission link is in a first condition and a second characteristic value when the status signal transmission link has been altered from a first condition to a second condition.

83 Claims, 9 Drawing Sheets

METHOD AND APPARATUS FOR SECURING AND/OR IDENTIFYING A LINK TO A PERCUTANEOUS PROBE

CROSS-REFERENCE TO RELATED APPLICATION

The present application claims priority to U.S. Provisional Application No. 60/325,975 filed Sep. 28, 2001 and incorporated herein in its entirety by reference.

BACKGROUND

The present invention relates generally to methods and apparatuses for securing and/or identifying a link to a percutaneous probe, such as an electrode used for electrical nerve stimulation. Electrical therapy has long been used in medicine to treat pain and other conditions. For example, transcutaneous electrical nerve stimulation (TENS) systems deliver electrical energy through electrode patches placed on the surface of a patient's skin to treat pain in the tissue beneath and around the location of the patches. One problem with TENS systems is that they may not provide patients with adequate relief. One approach to addressing this problem has been to deliver the electrical therapy percutaneously in a process termed "percutaneous neuromodulation therapy" (PNT) or "percutaneous electrical nerve stimulation" (PENS). This process can include inserting needle-like electrodes through the patient's skin to deliver electrical therapy more directly to the target nerves.

One method for applying percutaneous nerve stimulation is to insert acupuncture needles into the patient's skin and attach the needles to a wave form generator via cables and alligator clips to deliver percutaneous electrical currents. One drawback with this technique is that the acupuncture needles are typically exposed to the practitioner during insertion and removal. Accordingly, the practitioner can be exposed to blood-borne pathogens which might be present on the needle after the needle has been removed from the recipient.

SUMMARY

The present invention is directed to methods and apparatuses for securing and/or identifying a link to a percutaneous probe. An apparatus in accordance with one aspect of the invention includes an electrical coupler having a coupling member configured to be removably positioned at least proximate to a percutaneous probe. The coupling member can also be coupleable to a therapeutic electrical signal emitter. The apparatus can further include a therapeutic signal transmission link coupled to the electrical coupling member and coupleable to a source of therapeutic electrical signals to transmit the therapeutic signals to the recipient. The device can still further include a status signal transmission link at least proximate to the therapeutic signal transmission link and coupleable to a status signal emitter. The status signal transmission link can be at least tamper-resistant and/or tamper-evident, and can be configured to transmit a status signal having a first characteristic value when the status signal transmission link is in a first condition, and transmit a status signal having a second characteristic value different than the first characteristic value when the status signal transmission link has been altered from the first condition to a second condition.

In a further aspect of the invention, the status signal transmission link can include an electrical conductor, such as a stainless steel or fibrous carbon conductor, and the apparatus can further comprise a sensor coupled to the signal transmission link. The sensor can include at least one of an electrical continuity sensor, an electrical resistance sensor, and an electrical impedance sensor.

In another aspect of the invention, the apparatus can include a memory device having a stored characteristic value and positioned at least proximate to the therapeutic signal transmission link. The status signal transmission link can be connected to the memory device and can be connectable to a sensor to transmit the stored characteristic value from the memory device to the sensor.

The invention is also directed to a method for assessing compatibility between a percutaneous signal emitter and an electrical coupler configured to transmit electrical signals to a percutaneous probe. The method can include transmitting a status signal along a tamper-resistant and/or tamper-evident status signal transmission link coupled to the electrical coupler. The method can further include receiving a value of a characteristic of the status signal transmission link based on the status signal, and comparing the value with a target value for the characteristic. When the value differs from the target value by at least a pre-selected amount, the method can further include providing an indication to a user. The indication can include disabling the transmission of therapeutic electrical signals.

DETAILED DESCRIPTION

The present disclosure describes methods and apparatuses for securing and/or identifying a link between a therapeutic signal emitter and an electrical coupler that is operatively coupled to a percutaneous probe, such as an electrode. Accordingly, the apparatus can include a tamper-evident and/or tamper-resistant link between the therapeutic signal emitter and the electrical coupler. As a result, the apparatus can provide a signal to the user to indicate when the link to the electrical coupler is missing, inappropriate, damaged, and/or severed.

Many specific details of certain embodiments of the invention are set forth in the following description and in FIGS. 1–9 to provide a thorough understanding of these embodiments. One skilled in the art, however, will understand that the present invention may have additional embodiments, and that the invention may be practiced without several of the details described below.

Figure 1:
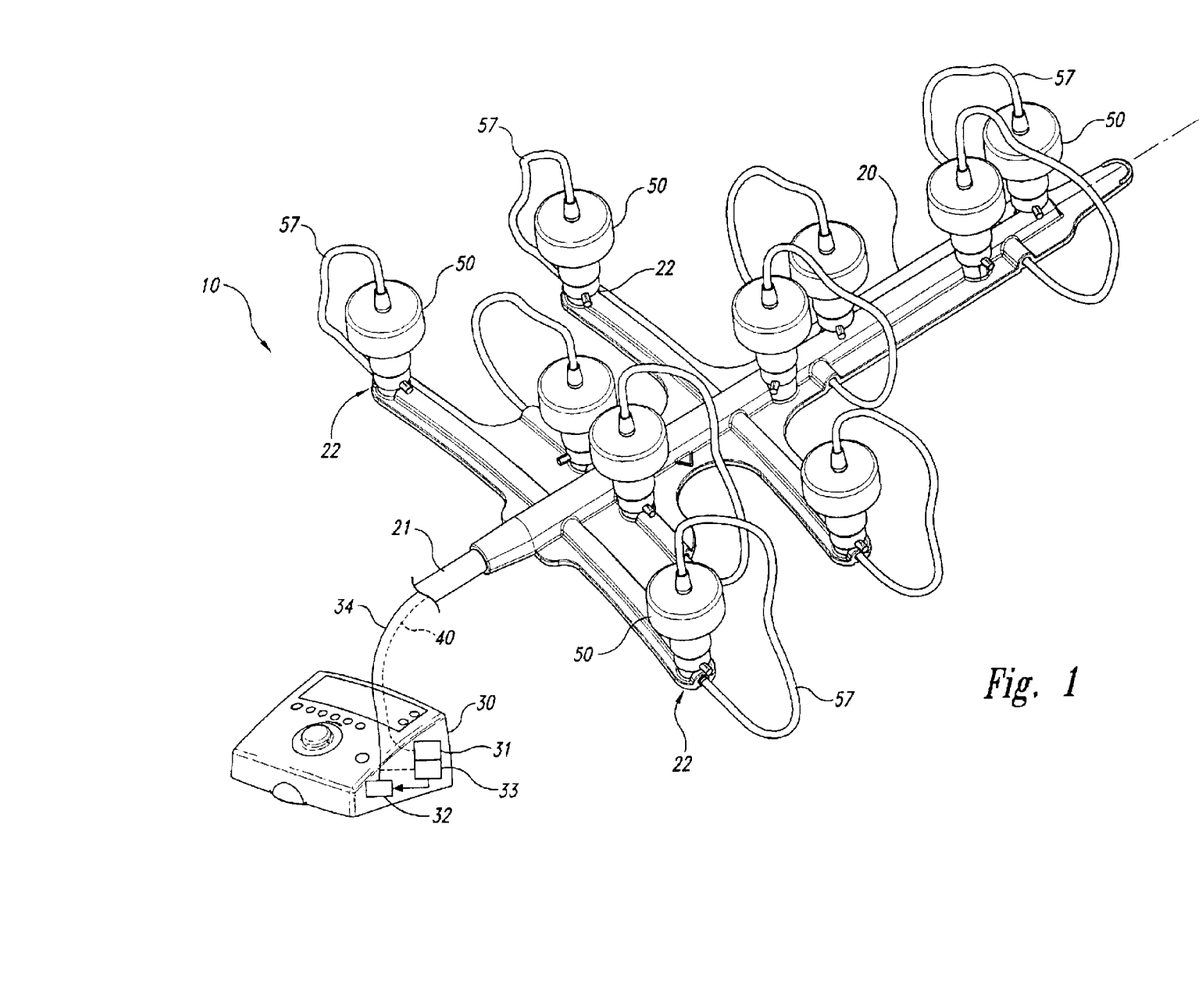
FIG. 1 is a partially schematic isometric view of an apparatus in accordance with an embodiment of the invention.

FIG. 1 is a partially schematic isometric illustration of an apparatus 10 in accordance with an embodiment of the invention. In one aspect of this embodiment, the apparatus 10 can include a control device 30 having a therapeutic signal emitter 32 configured to transmit therapeutic electrical signals along a therapeutic signal transmission link 34. The therapeutic signal transmission link 34 can include a plurality of electrical conductors, each connected to an electrical coupler 50 via a coupler cable 57. The electrical couplers 50 can be removably supported on a flexible support member 20. Accordingly, the support member 20 can include a plurality of support sites 22, each configured to support one of the electrical couplers 50. The electrical couplers 50 can be removed from the support member 20 and attached to percutaneous probes for delivering electrical therapy to a recipient, as described in greater detail below with reference to FIG. 2. Further details of embodiments of the support member 20 are included in U.S. patent application Ser. No. 09/751,382 titled "Apparatus and Method for Coupling Therapeutic and/or Monitoring Equipment to a Patient," filed Dec. 29, 2000 and incorporated herein by reference. Further details of embodiments of the control device 30 are included in the U.S. Provisional Application No. 60/325,725 titled "Method and Apparatus for Controlling Percutaneous Electrical Signals," filed Sep. 28, 2001 and incorporated herein by reference.

The apparatus 10 can further include a status signal transmission link 40 (shown in dashed lines in FIG. 1) connected between the support member 20 and the control device 30 to transmit status signals to and from the control device 30. The status signal transmission link 40 can be bundled together with the therapeutic signal transmission link 34 in a support member cable 21 to provide a compact link between the support member 20 and the control device 30.

The control device 30 can include status signal emitter 31 and a status signal sensor 33, both operatively coupled to the status signal transmission link 40. The status signal emitter 31 can direct status signals along the status signal transmission link 40, and the status signal sensor 33 can detect characteristics of the status signal transmission link 40 based upon the signals transmitted along the signal transmission link 40 by the status signal emitter 31. For example, the status signal transmission link 40 can include an electrical conductor and the status signal emitter 31 can transmit an electrical signal along the status signal transmission link 40. The status signal sensor 33 can detect a resistance, impedance and/or other electrical characteristic of the status signal transmission link 40, based on the electrical signal transmitted along the status signal transmission link 40. The status signal sensor 33 (and/or other components of the control device 30) can compare the measured value of the characteristic to an expected value and, if the measured value differs from the expected value by more than a pre-selected margin, the status signal sensor 32 (or other components) can provide an indication that the status signal transmission link 40 is missing or has been severed or damaged.

In one embodiment, the indication can include interrupting and/or preventing the therapeutic signal emitter 32 from transmitting therapeutic signals to the electrical couplers 50. In other embodiments, the indication can include a visual indication, such as an indicator light, display or sound. In any of these embodiments, the apparatus 10 can warn the user and/or restrict the user from using the apparatus 10 when it detects a damaged or missing status signal transmission link 40.

Figure 2:
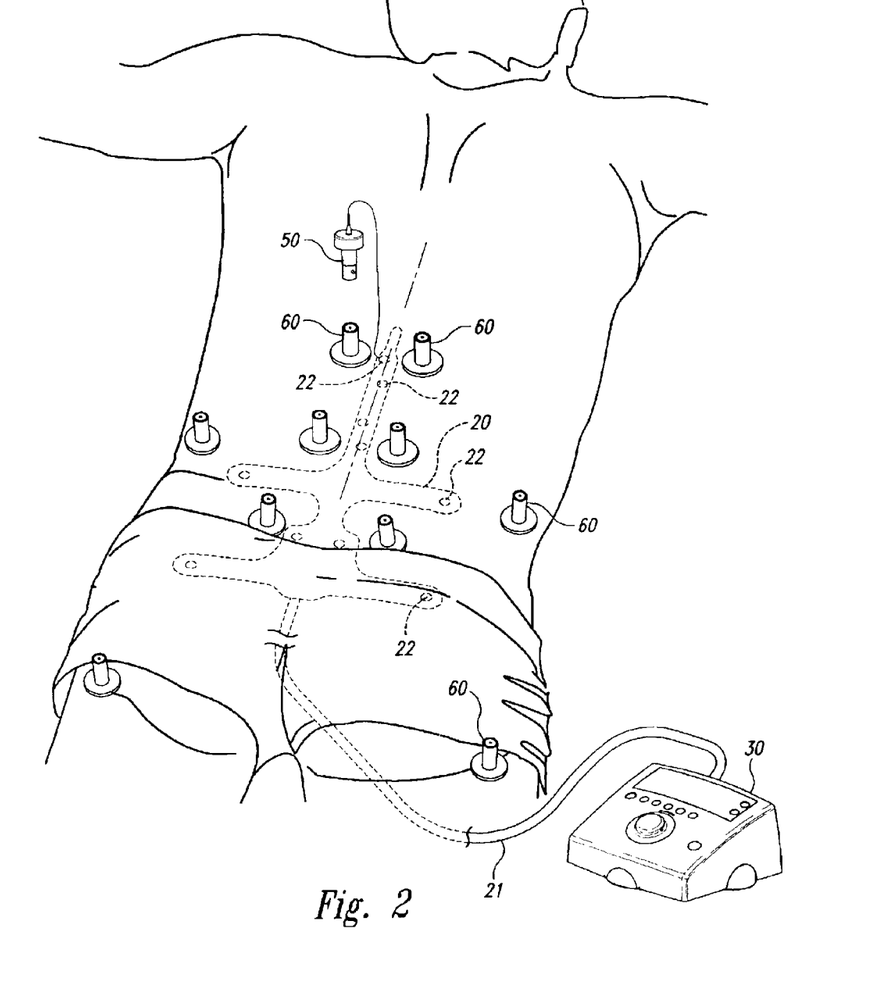
FIG. 2 is a partially schematic isometric view of an apparatus placed upon the back of a recipient in accordance with an embodiment of the invention.

FIG. 2 is a partially schematic, isometric illustration of the support member 20 placed upon a recipient's back in accordance with an embodiment of the invention. In one aspect of this embodiment, the support member 20 can include ten support sites 22, each removably carrying an electrical coupler 50 (one of which is shown in FIG. 2), and each aligned with an electrode assembly 60 removably positioned on the recipient's back. In other embodiments, the support member 20 can carry more or fewer electrical couplers 50, and/or the support member 20 can be configured to contact portions of the body other than the back. In any of the foregoing embodiments, the electrical couplers 50 can each be removed from the corresponding support site 22 and connected to the corresponding electrode assembly 60 to (a) insert a percutaneous probe from the electrode assembly 60 into the recipient in a shielded manner, and (b) provide electrical contact with the percutaneous probe, as described in greater detail below with reference to FIGS. 3–5.

Figure 3:
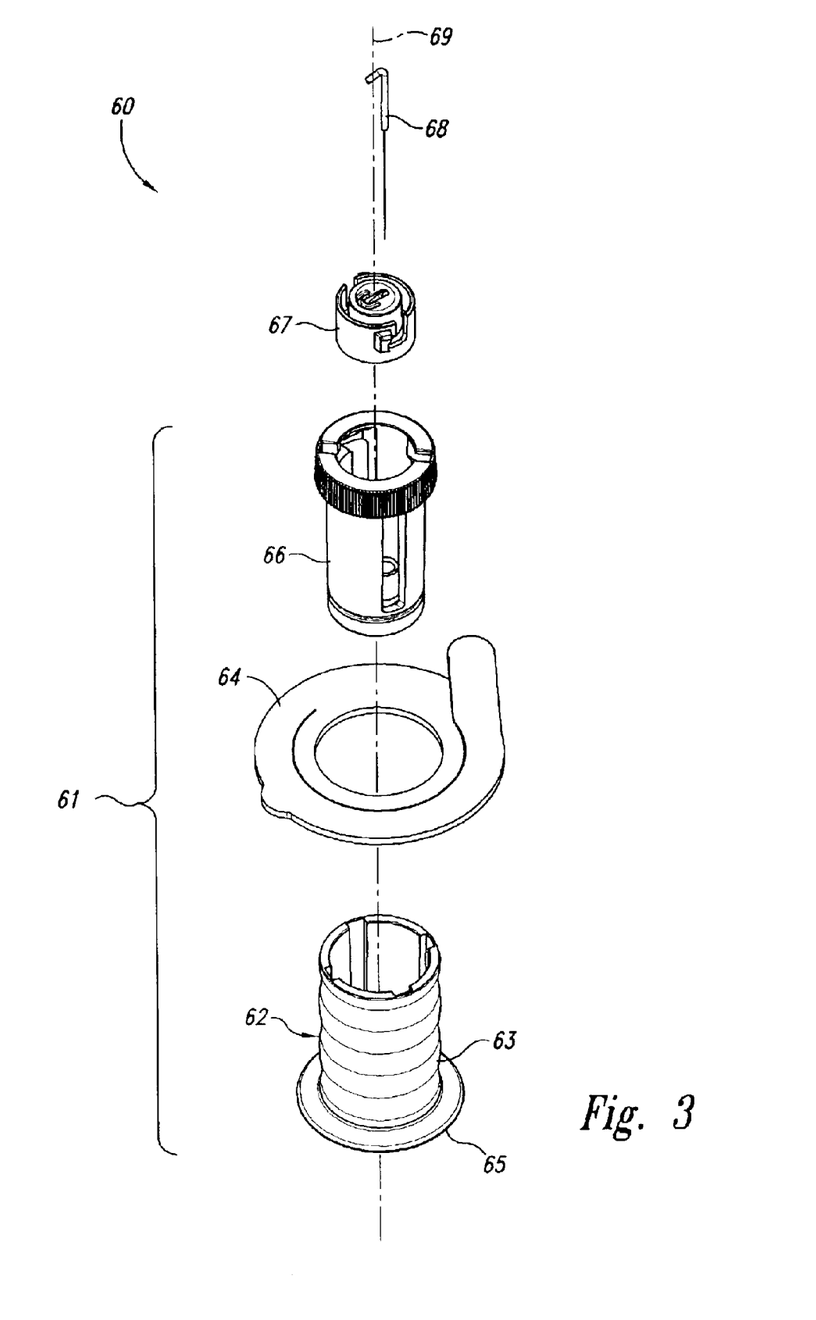
FIG. 3 is a partially exploded view of an electrode assembly in accordance with an embodiment of the invention.

FIG. 3 is an exploded isometric view of an embodiment of the electrode assembly 60 described above with reference to FIG. 2. The electrode assembly 60 can include a housing 61, which can in turn include a base 62 that rests on the recipient's skin, an adhesive pad 64 to adhere the base 62 to the skin, and a sleeve 66 received in the base 62. The base 62 can include a skin engaging surface and a casing. For example, the skin engaging surface can be an annular lip 65 and the casing can be a tube 63 projecting from the lip 64 at a desired angle. A slider 67 can fit in the sleeve 66 to support a percutaneous probe 68 (such as a sharpened electrode) for movement relative to the base 62 into and out of the recipient.

In operation, the slider 67 can slide downwardly and upwardly within the sleeve 66 to insert and retract the probe 68. In one aspect of this embodiment, the slider 67 and the sleeve 66 can rotate as a unit to selected positions relative to the base 62. In a further aspect of this embodiment, the slider 67, the sleeve 66, and the base 62 can all be coaxial with a central axis 69 of the housing 61, and the probe 68 can be offset or eccentric relative to the central axis 69. Accordingly, when the slider 67 and the sleeve 66 are rotated together as a unit relative to the base 62, the probe 68 orbits about the central axis 69 to a new position relative to the patient's skin surface. In an alternate embodiment, the probe 68 can be aligned on the central axis 69, and/or the sleeve 66 can be fixed relative to the base 62, for example, when it is not necessary to orbit the probe 68 about the central axis 69.

Figure 4:
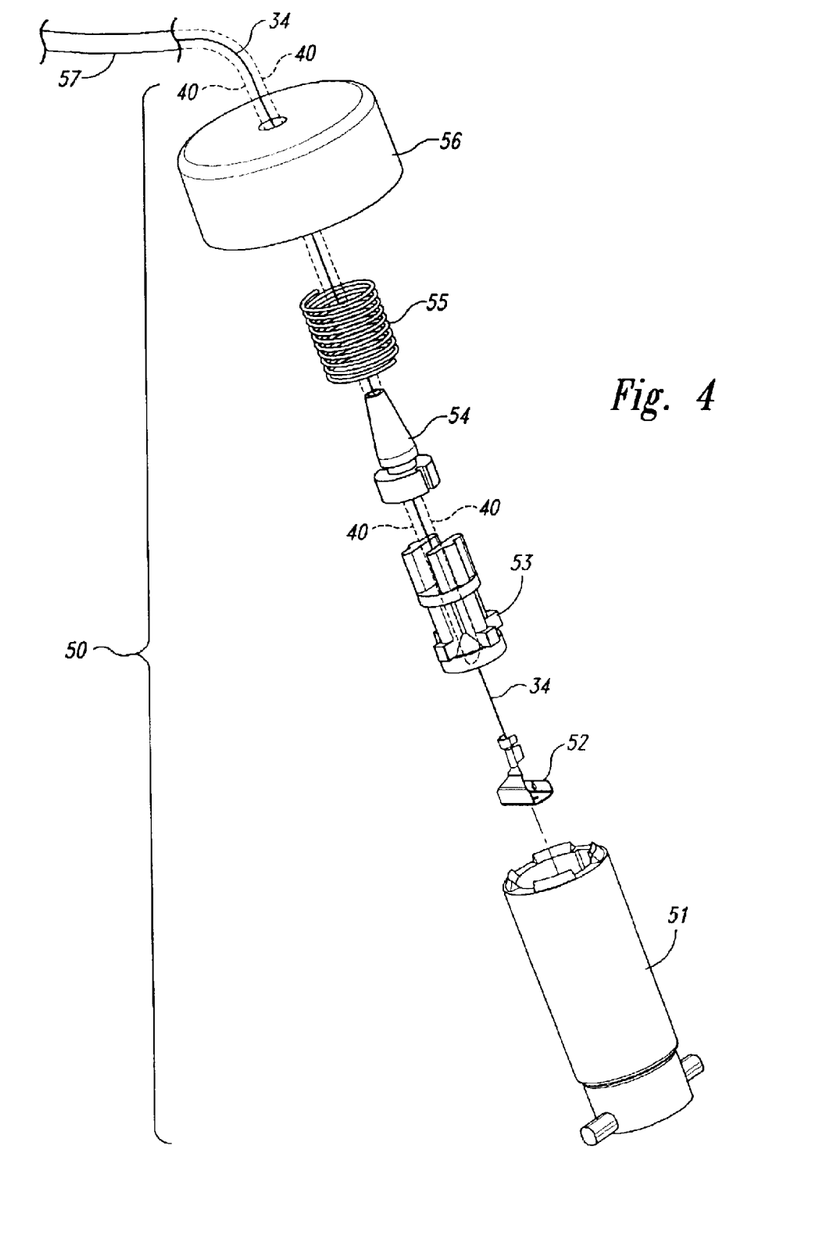
FIG. 4 is a partially exploded view of an electrical coupler for coupling to an electrode assembly in accordance with an embodiment of the invention.

FIG. 4 is an exploded top isometric view of an electrical coupler 50 that engages the slider 67 (FIG. 3) and moves the slider 67 and the probe 68 (FIG. 3) into the recipient. The electrical coupler 50 can include a plunger 51 that releasably engages the slider 67 and translates the slider 67 axially within the sleeve 66 (FIG. 3). The electrical coupler 50 can further include an electrical coupling member 52 supported by a support body 53. In one embodiment, the electrical coupling member 52 can be biased into direct contact with the probe 68 by a spring 55 to make electrical contact with the probe 68. Alternatively, the coupling member 52 can transmit electrical signals to the probe 68 without making direct contact with the probe 68, for example, via an intermediate dielectric material. In either embodiment, the coupling member 52 can be connected to the therapeutic signal link 34, housed within the coupler cable 57. The coupler cable 57 can pass through a cap 56 and a grommet 54 into the electrical coupler 50.

In one embodiment, the status signal transmission link 40 also can extend into electrical coupler 50. In one aspect of this embodiment, the status signal transmission link 40 can form a loop that terminates in the support body 53 proximate to the coupling member 52. In other embodiments, the status signal transmission link 40 can form a loop that terminates in other portions of the electrical coupler 50. In still further embodiments, the status signal transmission link 40 can form a loop that terminates at the support member 20 (FIG. 1) without being operatively coupled to the electrical coupler 50.

Figure 5:
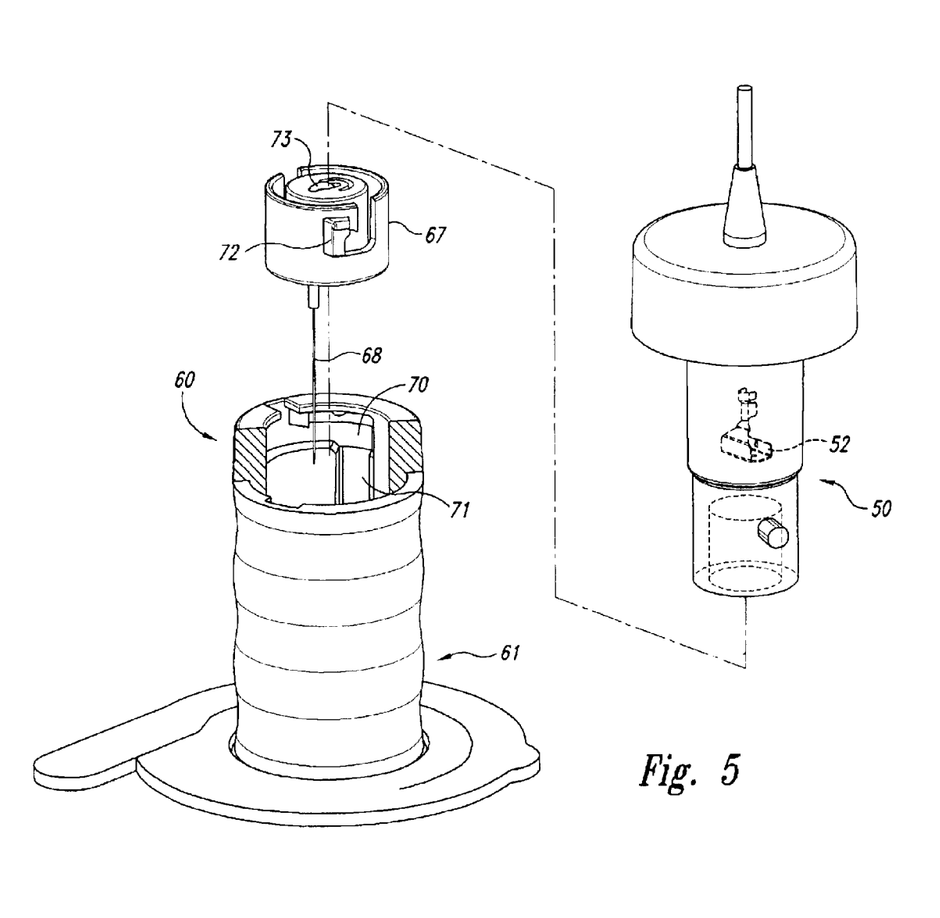
FIG. 5 is a partially exploded view of an electrical coupler positioned to actuate an electrode assembly in accordance with an embodiment of the invention.

FIG. 5 is a partially exploded isometric view of an embodiment of the electrical coupler 50 positioned to actuate the probe 68 of the electrode assembly 60. In one aspect of this embodiment, the slider 67 carrying the probe 68 can include a guide member 72 positioned for sequential movement in a transverse groove 70 and an axial groove 71 of the housing 61. The slider 67 can further include a receiving portion positioned to receive the electrical coupler 50 so that the coupling member 52 of the electrical coupler 50 makes electrical contact with an elbow portion 73 of the probe 68. The electrical coupler 50 can then be rotated and driven axially downwardly to insert the probe 68 into the recipient. When the probe 68 has been inserted, the user or practitioner can deliver therapeutic electrical signals to the recipient via the probe 68 by operating the control unit 30 (FIG. 1). Further details of embodiments of the electrical coupler 50 and the electrode assembly 60 are included in pending U.S. patent application Ser. Nos. 09/452,477 titled "Percutaneous Electrical Therapy System With Electrode Entry Angle Control," filed Dec. 1, 1999, and 09/666,931 titled "Method and Apparatus for Repositioning a Percutaneous Probe," filed Sep. 21, 2000, both incorporated herein in their entireties by reference.

In any of the foregoing embodiments, a feature of the electrode assembly 60 and the electrical coupler 50 in that they can be operated together to insert the probe 68 into the recipient without exposing the sharp end of the probe 68 to the practitioner or others who may be in the vicinity. Accordingly, the electrode assembly 60 and the electrical coupler 50 can reduce the likelihood for inadvertently pricking the practitioner and others with the probe 68, and can accordingly reduce the likelihood for transmitting bloodborne pathogens and/or other potentially harmful agents.

Figure 6:
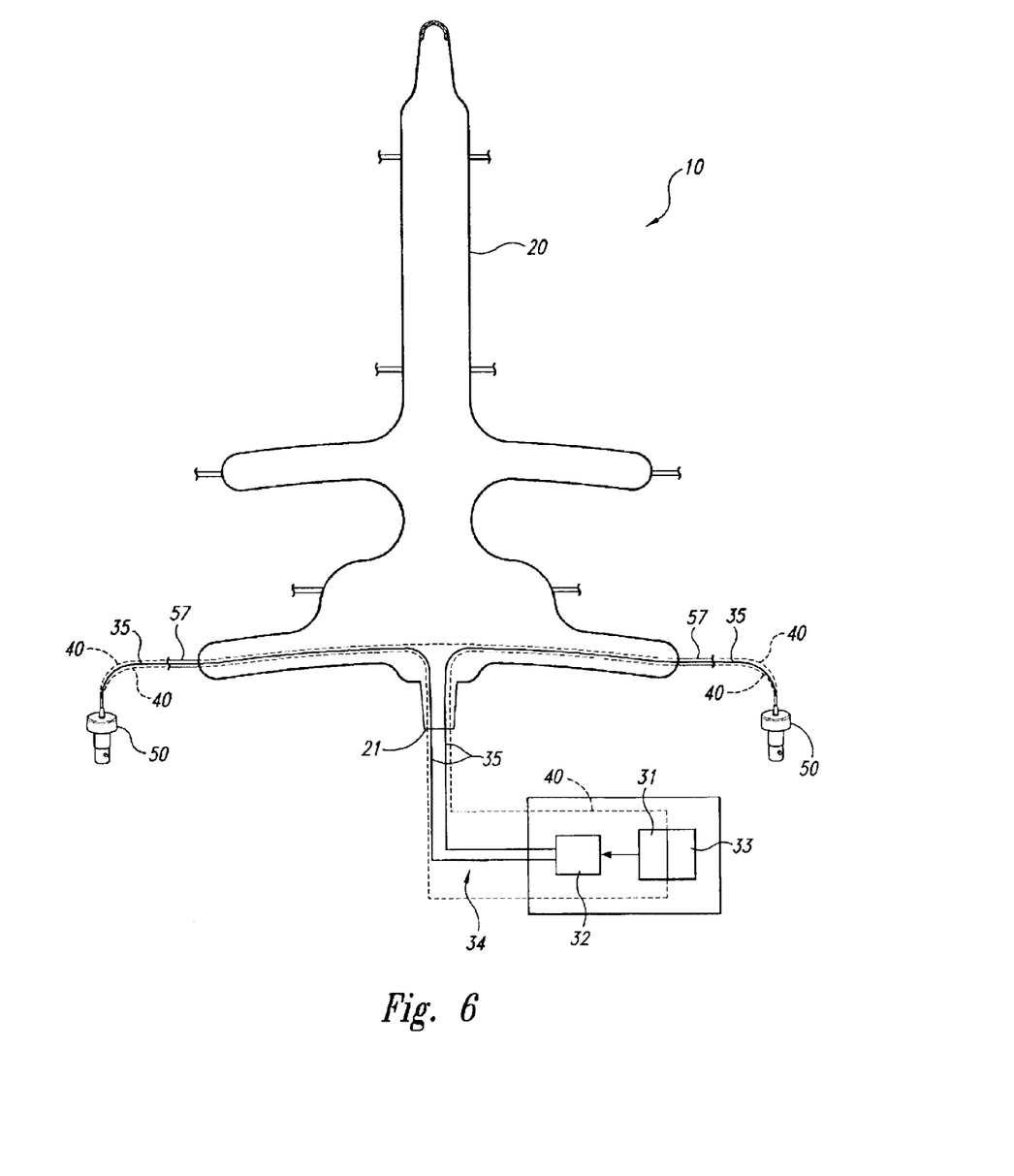
FIG. 6 is a partially schematic view of an apparatus generally similar to that shown in FIG. 1 having a status signal transmission link in accordance with an embodiment of the invention.
Figure 7:
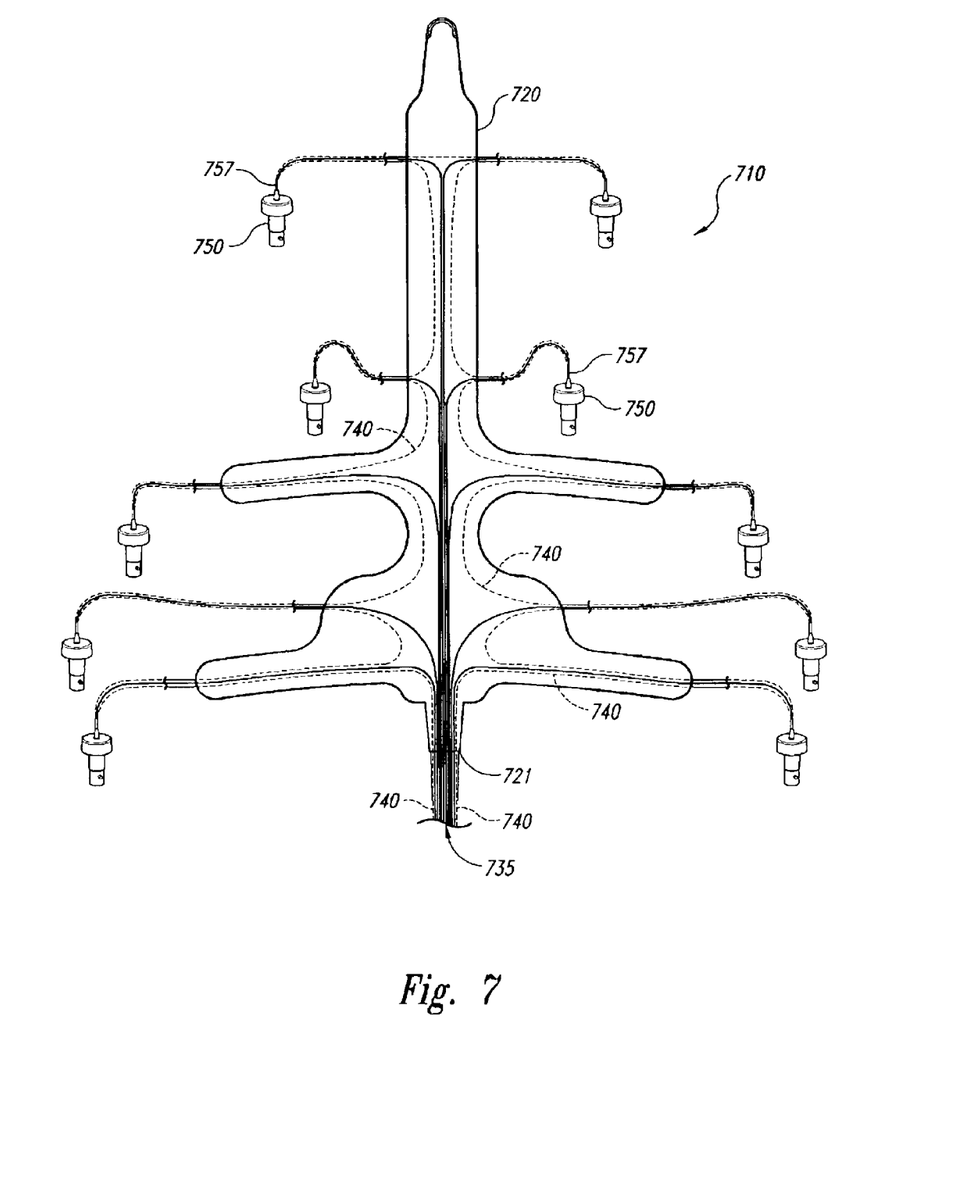
FIG. 7 is a partially schematic view of an apparatus having a status signal transmission link in accordance with another embodiment of the invention.

FIG. 6 is a partially schematic view of a portion of the apparatus 10 described above with reference to FIGS. 1–5. For purpose of illustration, only two of the ten electrode couplers 50 shown in FIG. 1 are shown in FIG. 6. Each electrical coupler 50 can be connected to the therapeutic signal emitter 32 via the therapeutic signal link 34. Accordingly, the therapeutic signal link 34 can include a plurality of electrical conductors 35 (two are shown in FIG. 6), each of which is connected to one of the electrical couplers 50, and each of which is electrically isolated from the other in the support member cable 21. In one aspect of this embodiment, each electrical conductor 35 can include a tamper-resistant and/or damage-resistant material. For example, each electrical conductor 35 can include a stainless steel wire or other conductor which is difficult to sever. In other embodiments, the electrical conductors 35 can include other materials that are also damage-resistant and/or tamper-resistant.

In a further aspect of this embodiment, the status signal transmission link 40 can include a loop that extends to two of the electrical couplers 50. For example, the status signal transmission link 40 can include an electrically conductive wire that extends from the status signal emitter 31, along the support member cable 21, out to one of the electrical couplers 50, back to the support member 20, out to the other electrical coupler 50, and back along the support member cable 21 to the status signal emitter 31 and/or electrical ground. Accordingly, the status signal transmission link 40 can form a normally closed, complete electrical circuit having a known characteristic, such as an impedance or resistance.

In operation, the status signal emitter 31 can direct a small current flow along the status signal transmission link 40, and the status signal sensor 33 can measure or detect the characteristic of the status signal transmission link 40 and compare the measured characteristic to an expected characteristic. If the measured characteristic differs from the expected characteristic by more than a pre-selected amount, the status signal sensor 33 can interrupt and/or prevent the transmission of therapeutic electrical signals along the therapeutic signal link 34. For example, if the status signal sensor 33 detects a break in the continuity of the normally closed circuit (indicating, for example, that the status signal transmission link 40 is missing or has been severed), or a substantial change in the impedance or resistance of the status signal transmission link 40 (indicating, for example, that the status signal transmission link 40 has been severed and reconnected), then the status signal sensor 33 can direct that the therapeutic signal emitter 32 be disabled from transmitting therapeutic signals along the therapeutic signal link 34.

In one embodiment, the status signal transmission link 40 can include a stainless steel wire or other conductor, which as described above, is both electrically conductive and resistant to severing. Stainless steel wire segments are also generally difficult to electrically reconnect without substantially altering the impedance of the circuit formed by the stainless steel wire. For example, stainless steel wires typically cannot be reconnected using conventional solder techniques, and twisting together the ends of a severed stainless steel wire will typically increase the impedance of the wire. Accordingly, reconnecting the status signal transmission link 40 (a) can be physically difficult and (b) can be difficult to do without altering the impedance of the status signal transmission link 40. As a result, the measured impedance of the signal transmission link 40 can indicate when the link 40 has been cut and reconnected.

In other embodiments, the status signal transmission link 40 can include other materials which are also (a) difficult to electrically reconnect and/or (b) difficult to reconnect without measurably altering the circuit impedance. Such materials include carbon fiber, which is (a) physically difficult to reconnect due to its fibrous structure, and (b) is difficult to reconnect without altering the overall impedance of the status signal transmission link. Other suitable materials include Kevlar® fiber with a conductive coating, and/or a plastic film or filament with a thin metal coating. In still further embodiments, the status signal transmission link 40 can include other materials that also resist being severed, change impedance when severed and reconnected, and/or are physically difficult to reconnect after being severed.

In yet further embodiments, the status signal transmission link 40 can conduct signals other than electrical signals. For example, the status signal transmission link 40 can include an optical fiber that transmits optical signals. The status signal emitter 31 can accordingly emit optical signals, and the status signal sensor 33 can accordingly detect changes in the characteristics of the status signal transmission link 40 by detecting changes in the signal transmitted along the link 40 when the link 40 is severed or severed and reconnected. In other embodiments, the status signal transmission link 40 can act as a wave guide and the status signal sensor 33 can detect signals reflected from discontinuities or breaks in the status signal transmission link 40, for example, using time domain reflectometry (TDR). In still further embodiments, the signal transmission link 40, the status signal emitter 31, and the status signal sensor 33 can have other arrangements.

One feature of the foregoing embodiments described above with reference to FIGS. 1–6 is that the status signal transmission link 40 can operate together with the status signal emitter 31 and the status signal sensor 33 to detect a break in the support member cable 21 and/or the coupler cable 57. An advantage of this arrangement is that the practitioner can be alerted to damage in either one of these cables and can correct the damage before administering therapy to the recipient and, in particular, before inserting the percutaneous probes 68 into the recipient.

Another feature of the foregoing embodiments described above with reference to FIGS. 1–6 is that the status signal sensor 33 can detect when the support member cable 21 and/or the coupler cables 57 have been severed and reconnected. For example, if a user were to sever one of the coupler cables 57 (including the conductor 35 and the signal transmission link 40), reconnect the severed ends of the signal transmission link 40 to each other, and connect the electrical conductor 35 to a device other than the electrical coupler 50 (such as an unprotected acupuncture needle), the status signal sensor 33 can detect this event and can halt the transmission of therapeutic electrical signals. Accordingly, this arrangement can detect when a user connects the control device 30 to percutaneous probes that lack the electrical coupler 50 originally attached to coupler cable 57. An advantage of this arrangement is that it can prevent or at least discourage the use of percutaneous probes that may not have the same safety features as embodiments of the electrode assembly 60 and the electrical coupler 50 described above. As a result, this arrangement can protect both patients and practitioners from potentially unsafe percutaneous therapy practices.

In other embodiments, the apparatus 10 can have other arrangements that include a tamper-resistant and/or tamper-evident status signal transmission link 40. For example, in one embodiment shown in FIG. 7, an apparatus 710 can include a support member 720 that removably supports a plurality of electrical couplers 750 in a manner generally similar to that described above with reference to FIG. 1. The support member 720 can be connected to a support member cable 721 that houses a corresponding plurality of electrical conductors 735, each connected to a corresponding one of the electrical couplers 750 via a corresponding plurality of coupler cables 757. The apparatus 710 can further include a status signal transmission link 740 that extends through the support member cable 721, along each coupler cable 757 in a series arrangement, and back along the support member cable 721. Accordingly, the status signal transmission link 740 can provide tamper-resistant and/or tamper-evident characteristics for each of the coupler cables 757 and the electrical couplers 750.

Figure 8:
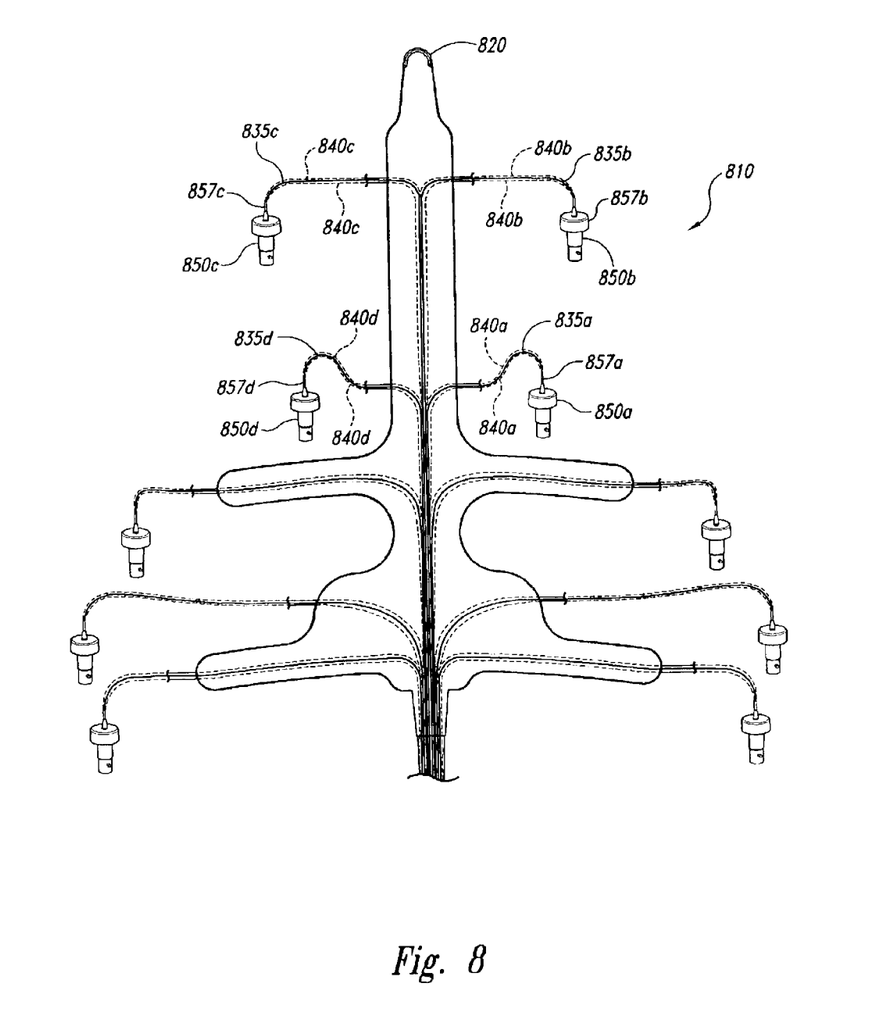
FIG. 8 is a partially schematic isometric view of an apparatus having a status signal transmission link arrangement in accordance with yet another embodiment of the invention.

FIG. 8 is a partially schematic illustration of an apparatus 810 having a plurality of status signal transmission links in accordance with another embodiment of the invention. In one aspect of this embodiment, the apparatus 810 can include a support member 820 that supports a plurality of electrical couplers 850 (four of which are identified in FIG. 8 as electrical couplers 850*a–d*) in a manner generally similar to that described above with reference to FIG. 1. The apparatus 810 can further include a corresponding plurality of coupler cables 857 (shown as couple cables 857*a–d*), each of which houses a corresponding electrical conductor 835 (shown as electrical conductors 835*a–d*). Each coupler cable 857 can also house a corresponding status signal transmission link 840 (shown as status signal transmission links 840*a–d*). Each status signal transmission link 840 can be separately connected to an individual status signal emitter and status signal sensor (not shown in FIG. 8). Accordingly, in the event of a fault with one of he coupler cables 857 or electrical couplers 850 an embodiment of the arrangement shown in FIG. 8 can narrow the location of the fault.

Figure 9:
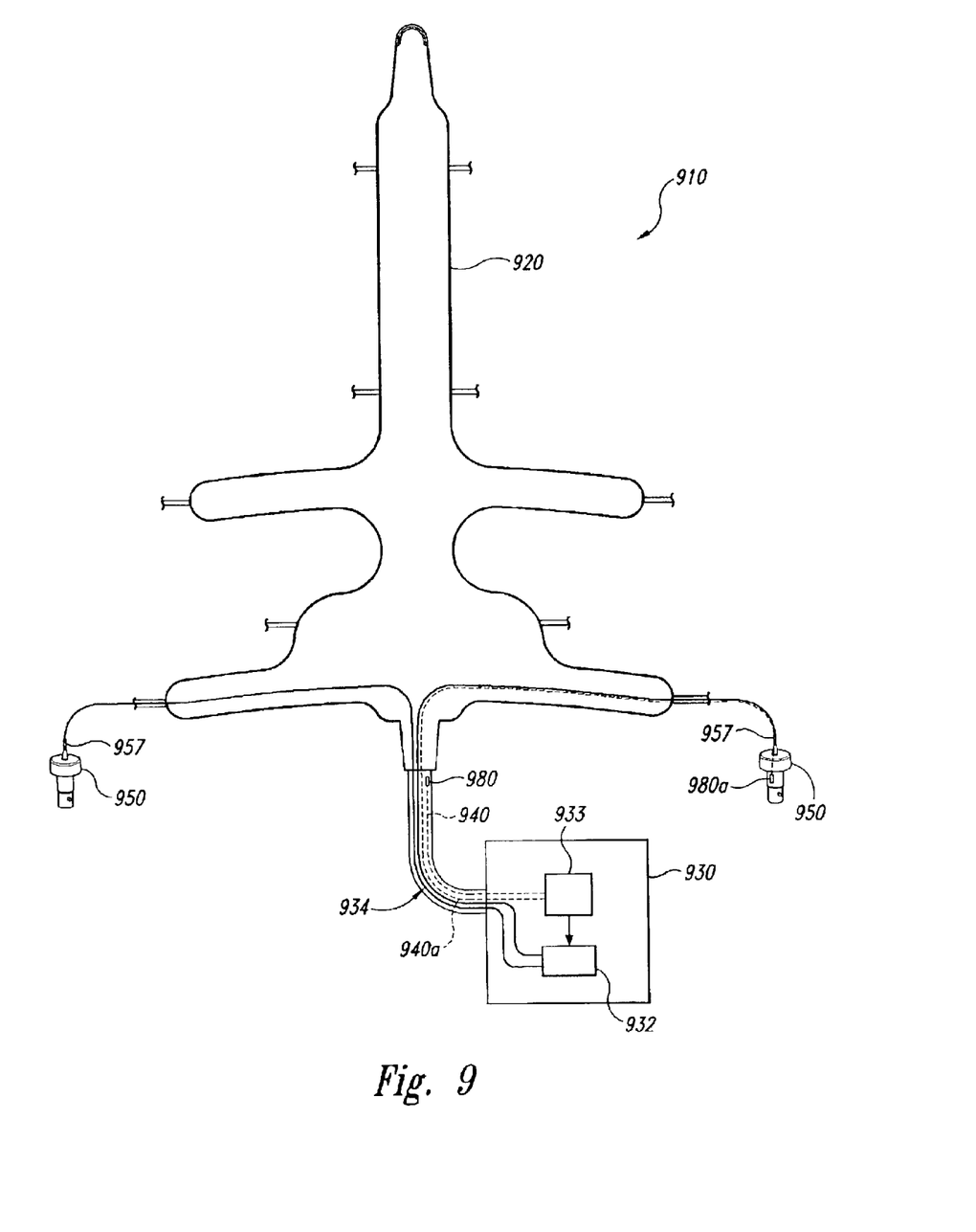
FIG. 9 is a schematic illustration of an apparatus having status signal transmission links coupled to one or more memory devices in accordance with further embodiments of the invention.

FIG. 9 is a partially schematic illustration of an apparatus 910 that includes a support member 920 having a support member cable 921 with an identity device 980 in accordance with another embodiment of the invention. In one aspect of this embodiment, the identity device 980 can include an integrated circuit chip that stores a pre-selected, unique identifier, such as a serial number. For example, the serial number can be the same for all support member cables 921 that are pre-determined to be compatible with a corresponding control device 930. Suitable identity devices 980 are manufactured by Maxim Integrated Products of Sunnyvale, Calif. and Dallas Semiconductor of Dallas, Tex. In other embodiments, the identity device 980 can have other configurations. In any of these embodiments, the identity device 980 can be coupled to a sensor 933 with a status signal transmission link 940. If the sensor 933 recognizes the identity of the identity device 980 as acceptable, the sensor 933 can allow a therapeutic signal emitter 932 to transmit electrical therapeutic signals to one or more electrical couplers 950 along a therapeutic signal link 934, in a manner generally similar to that described above. Alternatively, if the sensor 933 determines that the identity device 980 is missing or is not an appropriate device, the sensor 933 can interrupt and/or prevent signals from being transmitted from the therapeutic signal emitter 932.

In one aspect of the foregoing embodiments, the sensor 933 can check for both an identifier (such as a code or serial number) and an impedance of the status signal transmission link 940. In another aspect of these embodiments, at least one of these security features can be selectively deactivated. For example, the capability of the sensor 933 to check impedance can be deactivated when it is unnecessary, undesirable or uneconomical to include this feature. This feature can be selectively reactivated when appropriate.

In any of the foregoing embodiments, the identifier provided by the identity device 980 can be correlated with the type of support member 920. For example, one identifier can be correlated with a clavicular support member, and another identifier can be correlated with a lumbar support member. In other embodiments, the identifier can be correlated with other types of support members.

In an alternate arrangement, the apparatus 910 can include another identity device 980*a* positioned in an electrical coupler 950, in addition to or in lieu of the identity device 980 described above. The identity device 980a can be coupled to the sensor 933 with a status signal transmission link 940a. Accordingly, the sensor 933 can determine whether the identity device 980 is acceptable, unacceptable or missing. In other embodiments, the apparatus 910 can include identity devices having other locations, such as in the support member 920 or in coupler cables 957 connected between the support member 920 and the electrical couplers 950.

In any of the embodiments described above with reference to FIG. 9, a feature of these arrangements is that the sensor 933 can determine when an unauthorized percutaneous therapy device (such as a support member cable or electrical coupler) has been attached to the controller 930, by determining that the identity device 980 or 980a is missing or is an inappropriate device. As described above with reference to FIGS. 1–8, an advantage of this arrangement is that it can prevent practitioners from using the controller 930 with electrode assemblies and electrode couplers that lack the safety features described above with reference to FIGS. 2–5.

Nevertheless, it may be possible for a practitioner to circumvent the tamper-resistant and/or tamper-evident features of any of the foregoing devices described above with reference to FIGS. 1–9, despite the clear disincentives to do so. For example, a practitioner can severe the tamper-resistant and/or tamper-evident status signal transmission link coupled between a first (or original) electrical coupler and a status signal emitter and/or status signal sensor, provide a second (or replacement) electrical coupler in place of the first electrical coupler, and couple the status signal transmission link to the replacement electrical coupler. When the status signal transmission link includes an electrical conductor, the practitioner can reconnect the severed electrical conductor to the replacement electrical conductor by welding, brazing, melting, reflowing, crimping (for example, with a specialized tool) or otherwise processing the conductor to reestablish the connection between the status signal transmission link and the replacement electrical coupler without measurably altering the impedance of the circuit that includes the transmission link. In other embodiments, the practitioner may circumvent the status signal transmission link in other manners.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. An apparatus for administering percutaneous electrical therapy to a recipient, comprising:
   an electrical coupler having a coupling member configured to be removably positioned at least proximate to a percutaneous probe to transmit therapeutic electrical signals to the recipient, the coupling member further being coupleable to a source of therapeutic electrical signals;
   a therapeutic signal transmission link coupled to the coupling member and coupleable to a therapeutic electrical signal emitter; and
   a status signal transmission link at least proximate to the therapeutic signal transmission link and coupleable to a status signal emitter, the status signal transmission link being at least tamper-resistant and/or tamper-evident and being configured to transmit a status signal having a first characteristic value when the link is in a first condition, the status signal transmission link being configured to transmit a status signal having a second characteristic value different than the first characteristic value when the status signal transmission link has been altered from the first condition to a second condition.

2. The apparatus of claim 1, further comprising:
   a status signal emitter coupled to the status signal transmission link to direct the status signal to the transmission link; and
   a status signal sensor operatively coupled to the status signal transmission link to detect a change in a characteristic of the status signal transmission link.

3. The apparatus of claim 1 wherein the percutaneous probe is movably positioned within a housing, and wherein the electrical coupler includes an actuator releasable coupleable to the housing to move the percutaneous probe relative to the housing.

4. The apparatus of claim 1, further comprising:
   a housing; and
   a percutaneous probe carried by the housing and moveable relative to the housing between a first position and a second position, wherein the electrical coupler includes an actuator releasably coupleable to the housing and the probe to move the probe between the first position and the second position.

5. The apparatus of claim 1 wherein the therapeutic signal transmission link includes stainless steel.

6. The apparatus of claim 1 wherein the status signal transmission link includes an electrical conductor.

7. The apparatus of claim 1 wherein the status signal transmission link include an optical signal conduit.

8. The apparatus of claim 1 wherein the status signal transmission link includes stainless steel.

9. The apparatus of claim 1 wherein the status signal transmission link includes a fibrous carbon material.

10. The apparatus of claim 1 wherein the therapeutic signal transmission link includes an electrical conductor electrically isolated from the status signal transmission link, and wherein the status signal transmission link is bundled together with the electrical conductor.

11. The apparatus of claim 1, further comprising a sensor coupled to the status signal transmission link, and wherein the sensor includes at least one of an electrical continuity sensor, an electrical resistance sensor, and an electrical impedance sensor.

12. The apparatus of claim 1, further comprising a memory device coupled to the status signal transmission link, the memory device being configured to store a predetermined value and transmit the value via the status signal transmission link.

13. The apparatus of claim 1 wherein the status signal emitter is an electrical signal emitter, the electrical coupler is a first electrical coupler, and the coupling member is a first coupling member, and wherein the apparatus further comprises:
   a second electrical coupler having a second coupling member configured to be removably positioned at least proximate to a percutaneous probe to transmit therapeutic electrical signals to the probe;
   a coupler support member having a first support site configured to removably support the first electrical coupler, the coupler support member further having a second support site configured to removably support the second electrical coupler;
   a first electrical conductor connected between the first electrical coupler and the coupler support member;

a second electrical conductor connected between the second electrical coupler and the coupler support member, further wherein the signal transmission link is electrically conductive and includes stainless steel, carbon fiber, or both, and wherein the status signal emitter and the status signal transmission link form a normally closed electrical circuit, and a sensor coupled to the status signal transmission link and configured to detect a change in at least one of an impedance and a resistance of the circuit.

14. An apparatus for administering percutaneous electrical therapy to a recipient, comprising:

an electrical coupler having a coupling member, the coupling member being configured to be removably positioned at least proximate to a percutaneous probe to transmit therapeutic electrical signals to the recipient;

a therapeutic signal transmission link coupled to the coupling member and coupleable to a therapeutic electrical signal emitter;

a status signal emitter;

a status signal transmission link coupled between the status signal emitter and the electrical coupler; and a sensor operatively coupled to the status signal transmission link to detect a change in a characteristic of the status signal transmission link based on a signal emitted by the status signal emitter.

15. The apparatus of claim 14 wherein the status signal emitter is an electrical signal emitter, the electrical coupler is a first electrical coupler and the coupling member is a first coupling member, and wherein the apparatus further comprises:

a second electrical coupler having a second coupling member configured to be removably positioned at least proximate to a percutaneous probe to transmit therapeutic electrical signals to the recipient;

a coupler support member having a first support site configured to removably support the first electrical coupler, the coupler support member further having a second support site configured to removably support the second electrical coupler;

a first electrical conductor connected between the first electrical coupler and the coupler support member; and a second electrical conductor connected between the second electrical coupler and the coupler support member, further wherein the status signal transmission link is electrically conductive and includes stainless steel, carbon fiber, or both, and wherein the status signal emitter and the status signal transmission link form a normally closed electrical circuit; and wherein the sensor is configured to detect a change in at least one of an impedance and a resistance of the circuit.

16. The apparatus of claim 14 wherein the status signal transmission link includes an electrical conductor, and further wherein the status signal emitter is configured to emit electrical status signals and direct the electrical status signals to the status signal transmission link.

17. The apparatus of claim 14 wherein the status signal transmission link include an optical signal conduit, and further wherein the status signal emitter is configured to emit optical signals and direct the optical signals to the status signal transmission link.

18. The apparatus of claim 14 wherein the status signal transmission link includes stainless steel.

19. The apparatus of claim 14 wherein the status signal transmission link includes a fibrous carbon material.

20. The apparatus of claim 14 wherein the therapeutic signal transmission link includes an electrical conductor connected to the coupling member and coupleable to a source of therapeutic electrical signals, the electrical conductor being electrically isolated from the status signal transmission link, and wherein the status signal transmission link is bundled together with the electrical conductor.

21. The apparatus of claim 14 wherein the sensor includes an electrical continuity sensor.

22. The apparatus of claim wherein the sensor includes an electrical resistance sensor.

23. The apparatus of claim 14 wherein the sensor includes an electrical impedance sensor.

24. The apparatus of claim 14, further comprising a memory device coupled to the status signal transmission link, the memory device being configured to store a predetermined value and transmit the value via the status signal transmission link.

25. An apparatus for administering percutaneous electrical therapy to a recipient, comprising:

an electrical coupler having an electrical contact member positioned to engage a percutaneous probe;

a first electrical conductor coupled to the electrical contact member and coupleable to source of therapeutic electrical potential;

an electrical status signal emitter;

a status signal transmission link that includes a second electrical conductor coupled to the electrical coupler and the electrical status signal emitter, the second electrical conductor and the electrical status signal emitter defining a normally closed electrical circuit; and an electrical sensor coupled to the circuit, the electrical sensor being configured to detect a change in an electrical characteristic of the circuit.

26. The apparatus of claim 25 wherein the second electrical conductor includes stainless steel.

27. The apparatus of claim 25 wherein the second electrical conductor includes a fibrous carbon material.

28. The apparatus of claim 25 wherein the first and second electrical conductors are bundled together.

29. The apparatus of claim 25 wherein the sensor includes at least one of an electrical continuity sensor, an electrical resistance sensor, and an electrical impedance sensor.

30. The apparatus of claim 25, further comprising a housing carrying a percutaneous probe, the housing being configured to removably receive the electrical coupler, the electrical coupler being configured to connect to the percutaneous probe and move the percutaneous probe relative to the housing.

31. An apparatus for administering percutaneous electrical therapy to a recipient, comprising:

an electrical coupler support member having a first support site and a second support site;

a first electrical coupler removably supported at the first support site of the electrical coupler support member, the first electrical coupler having a first coupling member configured to be removably positioned at least proximate to a percutaneous probe to transmit therapeutic electrical signals to the recipient;

a second electrical coupler removably supported at the second support site of the electrical coupler support member, the second electrical coupler having a second coupling member configured to be removably positioned at least proximate to a percutaneous probe to transmit therapeutic electrical signals to the recipient;

an electrical cable coupled to the electrical coupler support member and the first and second coupling members, the electrical cable being configured to be coupled to a therapeutic signal emitter to transmit therapeutic signals to the first and second coupling members; and a status signal transmission link coupled to at least one of the electrical couplers and coupleable to a status signal emitter, the status signal transmission link being at least tamper-resistant, tamper-evident or both, the status signal transmission link being configured to transmit a status signal having a first characteristic value when the status signal transmission link is in a first condition, the status signal transmission link being configured to transmit a status signal having a second characteristic value different than the first characteristic value when the status signal transmission link has been altered from the first condition to a second condition.

32. The apparatus of claim 31, further comprising:

a status signal emitter coupled to the status signal transmission link; and a sensor operatively coupled to the status signal transmission link to detect a change in a characteristic of the status signal transmission link.

33. The apparatus of claim 31 wherein the electrical cable includes a first conductor coupled to the first electrical coupler and a second conductor coupled to the second electrical coupler, and wherein the status signal transmission link includes a third conductor configured to transmit signals independently of signals transmitted by the first and second conductors.

34. The apparatus of claim 31 wherein the status signal transmission link includes an electrical conductor.

35. The apparatus of claim 31 wherein the status signal transmission link include an optical signal conduit.

36. The apparatus of claim 31 wherein the status signal transmission link includes stainless steel.

37. The apparatus of claim 31 wherein the signal transmission link includes a fibrous carbon material.

38. The apparatus of claim 31, further comprising a sensor coupled to the status signal transmission link, and wherein the sensor includes at least one of an electrical continuity sensor, an electrical resistance sensor, and an electrical impedance sensor.

39. An apparatus for administering percutaneous electrical therapy to a recipient, comprising:

a therapeutic signal emitter configured to emit a selected therapeutic electrical signal;

a support member having at least one support site;

an electrical coupler removably supported at the at least one support site, the electrical coupler being electrically coupled to the therapeutic signal emitter to receive the selected therapeutic electrical signal, the electrical coupler being coupleable to a percutaneous probe;

a status signal emitter;

a status signal transmission link coupled between the status signal emitter and the electrical coupler to receive a status signal from the status signal emitter; and a sensor operatively coupled to the status signal transmission link to detect a change in a characteristic of the status signal transmission link.

40. The apparatus of claim 39 wherein the electrical coupler includes an electrical contact member positioned to connect to the percutaneous probe.

41. The apparatus of claim 39 wherein the status signal transmission link includes an electrical conductor.

42. The apparatus of claim 39 wherein the status signal transmission link include an optical signal conduit.

43. The apparatus of claim 39 wherein the status signal transmission link includes a stainless steel electrical conductor.

44. The apparatus of claim 39 wherein the status signal transmission link includes a fibrous carbon material.

45. The apparatus of claim 39 wherein the therapeutic signal transmission link includes an electrical conductor electrically isolated from the status signal transmission link, and wherein the status signal transmission link is bundled together with the electrical conductor.

46. The apparatus of claim 39, further comprising a memory device coupled to the status signal transmission link, the memory device being configured to store a predetermined value and transmit the value via the status signal transmission link.

47. An apparatus for administering percutaneous electrical therapy to a recipient, comprising:

an electrical coupler having a coupling member configured to be removably positioned at least proximate to a percutaneous probe, the coupling member further being coupleable to a therapeutic electrical signal emitter to transmit electrical signals to the percutaneous probe;

a therapeutic signal transmission link coupled to the coupling member and coupleable to the therapeutic electrical signal emitter;

a memory device having a stored characteristic value, the memory device being positioned at least proximate to the therapeutic signal transmission link; and a status signal transmission link connected to the memory device and connectable to a sensor to transmit the stored characteristic value from the memory device to the sensor.

48. The apparatus of claim 47 wherein the therapeutic signal transmission link and the memory device are housed in an electrical cable.

49. The apparatus of claim 47 wherein the memory device is carried by the electrical coupler.

50. The apparatus of claim 47, further comprising:

a control unit having the therapeutic electrical signal emitter; and a sensor housed in the control unit, the sensor being connected to the status signal transmission link to receive the stored characteristic value of the memory device, the sensor being operatively coupled to the therapeutic electrical signal emitter to control the transmission of signals from the therapeutic electrical signal emitter.

51. An apparatus for administering percutaneous electrical therapy to a recipient, comprising:

a first housing movably supporting a first percutaneous probe and having a first receiving portion;

a second housing movably supporting a second percutaneous probe and having a second receiving portion;

a therapeutic signal emitter configured to emit first and second therapeutic electrical signals;

a support member having first and second support sites;

a first actuator configured to be received by the first receiving portion of the first housing and move the first percutaneous probe relative to the first housing and into a recipient, the first actuator being electrically coupled to the therapeutic signal emitter to receive the first therapeutic electrical signal, the first actuator having a first electrical contact member configured to removably contact the first percutaneous probe;

a second actuator configured to be received by the second receiving portion of the second housing and move the second percutaneous probe relative to the second housing and into the recipient, the second actuator being electrically coupled to the therapeutic signal emitter to receive the second therapeutic electrical signal, the second actuator having a second electrical contact member configured to removably contact the second percutaneous probe;

an electrical status signal emitter;

an electrical status signal transmission link coupled between the status signal emitter and at least one of the first and second actuators; and an electrical sensor coupled to the status signal transmission link to detect a change in an electrical property of the status signal transmission link.

52. The apparatus of claim 51 wherein the signal transmission link includes stainless steel.

53. The apparatus of claim 51 wherein the signal transmission link includes a fibrous carbon material.

54. The apparatus of claim 51, further comprising:

a first electrical conductor coupled between the therapeutic signal emitter and the first electrical contact member and electrically isolated from the status signal transmission link;

a second electrical conductor coupled between the therapeutic signal emitter and the second electrical contact member and electrically isolated from the status signal transmission link; and wherein the status signal transmission link is bundled together with the first and second electrical conductors.

55. The apparatus of claim 51 wherein the electrical sensor includes at least one of an electrical continuity sensor, an electrical resistance sensor, and an electrical impedance sensor.

56. The apparatus of claim 51, further comprising a memory device coupled to the status signal transmission link, the memory device being configured to store a pre-determined value and transmit the value via the status signal transmission link.

57. A method for forming an apparatus for administering percutaneous electrical therapy, comprising:

providing an electrical coupler having a coupling member configured to be removably positioned at least proximate to a percutaneous probe inserted in a recipient, the coupling member further being coupleable to a source of therapeutic electrical signals to transmit the therapeutic electrical signals to the recipient;

connecting a therapeutic signal transmission link to the coupling member, the therapeutic signal transmission link being coupleable to a therapeutic electrical signal emitter; and coupling a tamper-resistant and/or tamper-evident status signal transmission link to the electrical coupler, the status signal transmission link being configured to transmit a status signal having a first characteristic value when the link is in a first condition, the status signal transmission link being configured to transmit a status signal having a second characteristic value different than the first characteristic value when the status signal transmission link has been altered from the first condition to a second condition.

58. The method of claim 57, further comprising selecting the status signal transmission link to include an electrical conductor.

59. The method of claim 57, further comprising selecting the status signal transmission link to include an optical signal conduit.

60. The method of claim 57, further comprising selecting the status signal transmission link to include stainless steel.

61. The method of claim 57, further comprising selecting the status signal transmission link to include a fibrous carbon material.

62. The method of claim 57, further comprising:

electrically isolating the therapeutic signal transmission from the status signal transmission link; and bundling the status signal transmission link together with the therapeutic signal transmission link.

63. The method of claim 57, further comprising coupling a sensor to the status signal transmission link, and wherein the sensor includes at least one of an electrical continuity sensor, an electrical resistance sensor, and an electrical impedance sensor.

64. The method of claim 57, further comprising coupling a memory device to the status signal transmission link, the memory device being configured to store a pre-determined value and transmit the value via the status signal transmission link.

65. A method for administering percutaneous electrical therapy to a recipient, comprising:

placing a coupling member of an electrical coupler in electrical communication with a percutaneous probe;

activating the electrical coupler to insert the percutaneous probe into the recipient;

coupling the coupling member to a therapeutic electrical signal emitter; and coupling a tamper-resistant and/or tamper-evident status signal transmission link to the electrical coupler, the status signal transmission link being configured to transmit a status signal having a first characteristic value when the link is in a first condition, the status signal transmission link being configured to transmit a status signal having a second characteristic value different than the first characteristic value when the status signal transmission link has been altered from the first condition to a second condition.

66. The method of claim 65, further comprising receiving an indication when the status signal transmission link has been altered from the first condition to the second condition.

67. The method of claim 65, further comprising receiving an indication that electrical signals from the therapeutic electrical signal emitter have been interrupted and/or halted when the status signal transmission link has been altered from the first condition to the second condition.

68. The method of claim 65 wherein coupling the status signal transmission link includes coupling an electrical conductor between the electrical coupler and a status signal emitter.

69. A method for assessing compatibility between a percutaneous signal emitter and an electrical coupler configured to transmit electrical signals to a percutaneous probe, the method comprising:

transmitting a status signal along a tamper-resistant and/or tamper-evident status signal transmission link coupled to the electrical coupler;

receiving a value of a characteristic of the status signal transmission link based on the status signal;

comparing the value with a target value for the characteristic; and when the value differs from the target value by at least a pre-selected amount, providing an indication to a user.

70. The method of claim 69 wherein the signal transmission link is electrically conductive and wherein transmitting a status signal includes applying a current to the signal transmission link.

71. The method of claim 69 wherein the signal transmission link is optically conductive and wherein transmitting a status signal includes applying an optical signal to the signal transmission link.

72. The method of claim 69 wherein providing an indication to the user includes disabling transmission of therapeutic electrical signals.

73. The method of claim 69 wherein providing an indication to the user includes at least restricting the user from transmitting therapeutic signals to the percutaneous probe.

74. The method of claim 69 wherein transmitting a status signal along a tamper-resistant and/or tamper-evident status signal transmission link includes transmitting a status signal along a status signal transmission link that is coupled to an electrical coupler of the percutaneous probe.

75. The method of claim 69 wherein receiving a value of a characteristic includes receiving a signal from a memory device coupled to the status signal transmission link.

76. A method for replacing an electrical coupler for a status signal transmission percutaneous probe, comprising:

severing a tamper-resistant and/or tamper-evident status signal transmission link coupled to a first electrical coupler of a percutaneous probe by separating a first portion of the status signal transmission link coupled to the first electrical coupler from a second portion of the status signal transmission link coupleable to a source of status signals;

providing a second electrical coupler in place of the first electrical coupler; and coupling the second portion of the status signal transmission link to the second electrical coupler.

77. The method of claim 76 wherein the status signal transmission link includes a stainless steel conductor and severing the signal transmission link includes severing the stainless steel conductor, and wherein the method further includes connecting the stainless steel conductor to the second coupler.

78. The method of claim 76 wherein the signal transmission link includes a carbon fiber conductor and severing the status signal transmission link includes severing the carbon fiber conductor, and wherein the method further includes connecting the carbon fiber conductor to the second coupler.

79. The method of claim 76 wherein the status signal transmission link is coupleable to a sensor to detect a change in a characteristic of the link, the characteristic having a first value when the link is coupled to the first electrical coupler, and wherein the method further comprises providing the link with a second value of the characteristic when the link is coupled to the second electrical coupler, the second value being at least approximately the same as the first value.

80. A method for assessing compatibility between a therapeutic signal emitter and a therapeutic signal transmission link, the therapeutic signal transmission link being connected to an electrical coupler configured to transmit electrical signals to a percutaneous probe, the method comprising:

receiving, via a status signal transmission link, a signal from a memory device positioned at least proximate to the therapeutic signal transmission link;

comparing the signal received from the memory device to a target signal; and when the signal received from the memory device differs from the target signal by at least a pre-selected amount, providing an indication to a user.

81. The method of claim 80 wherein providing an indication to the user includes interrupting and/or preventing therapeutic electrical signals from being transmitted along the therapeutic signal transmission link.

82. The method of claim 80 wherein receiving a signal from a memory device includes receiving a signal from an integrated circuit device.

83. The method of claim 80 wherein receiving a signal from a memory device includes receiving a signal from an integrated circuit device positioned in at least one of the electrical coupler and a cable extending between the electrical coupler and the therapeutic signal emitter.

* * * * *